United States Patent [19]

Zor et al.

[11] Patent Number: 4,670,426

[45] Date of Patent: Jun. 2, 1987

[54] INTERRUPTION OF FERTILITY IN MAMMALS BY POST-COITAL PILLS

[75] Inventors: Uriel Zor, Rehovot; Shalom Joseph, Ramat Gan, both of Israel

[73] Assignee: Yeda Research and Development Co., Ltd., Rehovot, Israel

[21] Appl. No.: 672,716

[22] Filed: Nov. 19, 1984

Related U.S. Application Data

[63] Continuation-in-part of Ser. No. 581,023, Feb. 16, 1984, abandoned.

[30] Foreign Application Priority Data

Mar. 24, 1983 [IL] Israel ......................................... 68222

[51] Int. Cl.⁴ ............................................. A61K 31/56
[52] U.S. Cl. .................................... 514/171; 514/178; 514/843
[58] Field of Search ......................... 514/170, 171, 178

[56] References Cited

U.S. PATENT DOCUMENTS

| 4,386,085 | 5/1983 | Teutsch et al. | 260/239.5 |
| 4,459,235 | 7/1984 | Chinn et al. | 260/397.5 |
| 4,536,401 | 8/1985 | Neef et al. | 260/397.4 |

OTHER PUBLICATIONS

Cunningham et al., "J. Clin. Endocrinol. Met." (1975), vol. 40 (2), pp. 265–267, an article titled—"Antiovulatory Activity of Synthetic Corticoids" as abstracted in Chem. Abs. 82 (25), par. 165,224(g).

*Primary Examiner*—Leonard Schenkman
*Assistant Examiner*—Joseph A. Lipovsky
*Attorney, Agent, or Firm*—Browdy and Neimark

[57] ABSTRACT

There are provided post-coital contraceptive pharmaceutical compositions comprising a blocker of progesterone activity (antiprogesterone) at comparatively high dosage, or a combination of such blocker of progesterone activity with a blocker of estrogen and of progesterone synthesis.

3 Claims, No Drawings

INTERRUPTION OF FERTILITY IN MAMMALS BY POST-COITAL PILLS

RELATION TO OTHER PATENT APPLICATIONS

The present application is a continuation-in-part to U.S. patent application Ser. No. 581,023, now abandoned, filed Feb. 16, 1984.

FIELD OF THE INVENTION

There are provided pharmaceutical compositions for use as post-coital contraceptives. These contain as active ingredient either an effective dosage of a blocker of progesterone activity, or a combination of such blocker with a blocker of estrogen and of progesterone synthesis.

BACKGROUND OF THE INVENTION

Nowadays there are widely used contraceptive drugs based on the derivatives of estrogens and progesterones. These female steroid hormone combinations prevent pituitary gonadotropin release, thus preventing ovulation and subsequent fertilization. Pills of this type are taken 20 days per month and are quite safe and effective in preventing pregnancy. Sometimes undesired, and even quite serious side-effects are encountered. Recently also other drugs have been introduced for this purpose, such as a gonadotropin releasing hormone, which is effective in males and females by direct action on the gonads; prostaglandins which contract the uterine muscle and thus induce abortion; and antiprogesterone which competes with progesterone at its receptor and thus induces abortion. Each of the above contraceptive preparations has some limitations and sometimes rather severe side-effects or complications are encountered.

SUMMARY OF THE INVENTION

The contraceptive compositions of the invention are based on an effective quantity of a blocker of progesterone activity (antiprogesterone) or on a combination of such a blocker in combination with an inhibitor of synthesis of estrogen and progesterone. The compositions of the invention contain an antiprogesterone, i.e. an antagonist to the progesterone receptor. Typical compounds of this type are fluocinolone acetonide (FA), triamcinolone acetonide (TA), steroids having a cyclic 16,17-acetal with acetone and 17$\beta$-hydroxy, 11$\beta$-(4-dimethylaminophenyl-1, 17$\alpha$-propyl-ynyl)-estra-4,9-dien-3-one, designated as RU-486 by Roussel Uclaf, and equivalent derivatives. Compounds such as FA and TA are effective when used by themselves, the dosage being in the range of 20 to 100 mg per person per day, and preferably in the range of 40 to 60 mg per person per day.

An enhanced effect is attained when a compound of the type defined above (such as TA, FA, R-486) or the like is used in combination with inhibitor of progesterone synthesis.

Side-chain cleavage enzyme and 3$\beta$-ol-dehydrogenase are enzymes involved in the synthesis of P$_4$. When inhibitors of these enzymes are administered, this brings about an indirect inhibition of progesterone synthesis. Compounds which block P$_4$ synthesis are aminoglutethimide (AG), 2$\alpha$-cyano-4,4,17$\alpha$-trimethyl-5-androst-5-en-17$\beta$-ol-3-one, (cyanoketone), 20,25-diazocholesterol and compounds having an equivalent activity. It is apparent that coadministration of the two ingredients together result in a synergistic effect.

Compositions for human use, comprising in combination a compound such as TA or FA together with an inhibitor or progesterone synthesis generally comprise about 10 to 50 mg of the TA or FA type compound in combination with about 300 to 1000 mg of the AG type compound per person.

Experiments with rats have shown that AG by itself at a dosage of 100 mg/kg was ineffective.

Experiments have shown that compositions containing 2 mg/kg TA and 50 or 100 mg/kg AG prevented pregnancy in 40% and 90% respectively. TA alone at 2 mg/kg gave also a 40% pregnancy reduction. TA alone at 5 mg/kg gave a maximal response (95% pregnancy reduction).

It has been found that the most advantageous ratio of TA/AG is about 1:50 for a maximum effect when both are used together.

Experiments have shown that the combination of TA, FA and the like compounds with AG type compounds is effective when applied anytime during the first week after intercourse, provided the drug is administered for 3 days. The drugs ought to be applied as soon as possible after intercourse or during the expected menstrual period, and the application is best continued for from 2 to 6 days. Application can be by injection and also by the oral route. These results were obtained with rats.

The contraceptives according to the invention are effective in the interruption of nidation and thus prevent pregnancy in mammals, and especially in humans. The glucocorticosteroids such as TA act as competitive blockers of the binding of progesterone to its own receptor. AG is widely used in the treatment of breast cancer, while TA is used as an antiinflammatory steroid.

The basis of the activity of the novel drug is the well established role of estrogen and progesterone in ovum implantation (nidation) and vice versa, namely that elimination of a large precentage of estrogen and progesterone (of the order of 90 percent or more) prevents uterine implantation of the fertilized ova, and thus pregnancy.

The following examples for human use, of compositions according to the invention are to be construed in an illustrative sense:

EXAMPLE 1

Triamcinolone acetonide: 50 mg

EXAMPLE 2

Aminogluthetimide (AG): 500 mg
Triamcinolone acetonide (TA): 20 mg

EXAMPLE 3

Aminogluthetimide: 500 mg
Fluocinolone acetonide: 30 mg

EXAMPLE 4

R-486: 50 mg
Aminogluthetimide: 500 mg

Further contraceptive compositions were prepared which contained inhibitors of side chain cleavage enzyme and inhibitors of 3$\beta$-ol-dehydrogenase and an inhibitor of progesterone activity.

All the pharmaceutical compositions tested proved to be effective in the prevention of pregnancy with a high degree of efficacy, both with laboratory animals and with higher primates. The same effect was attained with an effective dosage of progesterone antagonist and with combinations of same at a lower dosage with a blocker of progesterone and estrogen synthesis.

We claim:

1. A pharmaceutical composition having post-coital contraceptive activity containing, as active ingredients, an effective quantity of progesterone antagonist in combination with a blocker of synthesis of estrogen and of progesterone, the weight ratio of said progesterone antagonist to said blocker of the synthesis of estrogen and progesterone being about 1:50, and said progesterone antagonist being triamcinolone acetonide and said blocker of the synthesis of estrogen and of progesterone being aminogluthetimide.

2. A method of post-coital contraception comprising post-coitally administering to a human female a pharmaceutical composition comprising, as active ingredient, an effective quantity of a progesterone antagonist in combination with a blocker of the synthesis of estrogen and progesterone, wherein the weight ratio of said progesterone antagonist to said blocker of the synthesis of estrogen and progesterone is about 1:50, said progesterone antagonist being triamcinolone acetonide and said blocker of the synthesis of estrogen and progesterone being aminogluthetimide.

3. A method according to claim 2 wherein said administration of progesterone antagonist is at a 10–50 mg daily dosage and said administration of said blocker of the synthesis of estrogen and progesterone is at a 300–1000 mg daily dosage.

* * * * *